United States Patent [19]

Montavon et al.

[11] 4,348,518

[45] Sep. 7, 1982

[54] CEPHALOSPORINS

[75] Inventors: Marc Montavon; Roland Reiner, both of Basel, Switzerland

[73] Assignee: Hoffmann-La Roche Inc., Nutley, N.J.

[21] Appl. No.: 873,446

[22] Filed: Jan. 30, 1978

Related U.S. Application Data

[62] Division of Ser. No. 586,677, Jun. 13, 1975, Pat. No. 4,091,211.

[30] Foreign Application Priority Data

May 5, 1974 [CH] Switzerland .......................... 5743/75
May 29, 1974 [CH] Switzerland .......................... 6915/75
Jun. 21, 1974 [CH] Switzerland .......................... 8537/74

[51] Int. Cl.³ ................ C07D 501/36; C07D 501/18
[52] U.S. Cl. ...................................... 544/026; 544/27; 544/21; 424/246
[58] Field of Search .................... 544/26, 27, 21; 424/246

[56] References Cited

U.S. PATENT DOCUMENTS 3,278,531 10/1966 Cox et al. .......................... 260/243
3,530,123 9/1970 Takano et al. ...................... 260/243
3,867,380 2/1975 Dunn et al. ......................... 260/243
3,962,232 6/1976 Koppel .............................. 260/243
4,018,921 4/1977 Gleason ............................. 544/26

FOREIGN PATENT DOCUMENTS 798209 10/1973 Belgium .
863751 2/1978 Belgium .
823657 9/1969 Canada .
2225694 12/1972 Fed. Rep. of Germany .
2356704 2/1974 Fed. Rep. of Germany .
2461478 2/1976 Fed. Rep. of Germany .
2534071 2/1976 Fed. Rep. of Germany .

Primary Examiner—Nicholas S. Rizzo
Attorney, Agent, or Firm—Jon S. Saxe; George M. Gould; William H. Epstein

[57] ABSTRACT

Cephalosporins represented by the formula

X—S—Y wherein X is a deacetoxycephalosporinyl group and Y is a 6-membered heterocyclic group containing 1–3 nitrogens at least one of which is substituted and at least one of which is adjacent to a carbonyl group, said heterocyclic group containing one or more ring substituents and being characterized by being non-aromatic and non enolizable to an aromatic form.

13 Claims, No Drawings

CEPHALOSPORINS

CROSS REFERENCE TO RELATED APPLICATION

This application is a divisional application of U.S. Application Ser. No. 586,677, filed June 13, 1975, now U.S. Pat. No. 4,091,211, issued May 23, 1978.

DETAILED DESCRIPTION OF THE INVENTION

The present invention is directed to cephalosporins represented by the general formula $$X-S-Y$$

wherein X is a deacetoxycephalosporinyl group and Y is a 6-membered heterocyclic group containing 1-3 nitrogens at least one of which is substituted and at least one of which is adjacent to a carbonyl group, said group containing one or more ring substituents and being characterized by being non-aromatic and not enolizable to an aromatic form and pharmaceutically acceptable salts and hydrated forms thereof.

A preferred group of compounds in accordance with the present invention are those wherein X in formula I is a group represented by the formula

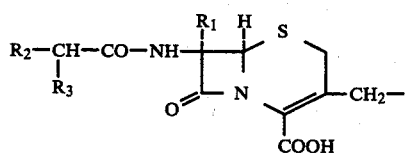

wherein $R_1$ is hydrogen or methoxy, $R_2$ is cyano, or a pyridylthio, aliphatic, alicyclic, aromatic or hetero aromatic group which may be substituted with one or more members of the group consisting of hydroxy, halo, lower alkyl or lower alkoxy groups and $R_3$ is hydrogen, hydroxy, hydroxymethyl, amino, azido, carboxy or sulfo and, when $R_2$ is a pyridylthio group, $R_3$ is hydrogen.

As used herein, the term "halogen" denotes chlorine, fluorine or bromine, chlorine being preferred. As used herein, the term "aliphatic group" includes both straight and branched chain alkyl and alkenyl groups with up to 6 carbon atom such as, for example, methyl, ethyl, propyl, isopropyl, n-butyl, isobutyl, pentyl, hexyl and the like, vinyl, propenyl, butenyl, pentenyl, hexenyl and the like; the alkyl groups with 4 carbon atoms, particularly n-butyl and isobutyl, being preferred. The term "alicyclic group" denotes saturated or unsaturated, non-aromatic groups containing from 3 to 6 carbon atoms such as, for example,, cyclopropyl, cyclobutyl, cyclopentyl, cyclohexyl, cyclohexenyl, cyclohexadienyl and the like; the groups containing 6 carbon atoms, particularly cyclohexyl and cyclohexadienyl, being preferred. As used herein, the term "aromatic group" relates to phenyl, phenyl-$C_{1-3}$-alkyl and phenoxy-$C_{1-3}$-alkyl, wherein the phenyl and/or the alkyl moiety may be substituted with one or more members of the group consisting of hydroxy, halo, lower alkyl or lower alkoxy; phenyl and p-hydroxyphenyl being preferred. The term "heteroaromatic group" relates to 5- or 6-membered aromatic groups containing 1-4 nitrogen atoms and/or one oxygen or sulfur atom such as for example, sydnonyl, tetrazolyl, furyl, thienyl, pyrazolyl, pyrrolyl, thiazolyl, isothiazolyl, oxazolyl, isoxazolyl and the like, pyridyl, pyrimidinyl, pyrazinyl, pyridazinyl, triazinyl and the like; the 5-membered groups, particularly thienyl, furyl, tetrazolyl, triazolyl, pyrazolyl and sydnonyl being preferred.

Most preferred compounds in accordance with the invention are those in which $R_2$ is cyano, 2-thienyl, 2-furyl, phenyl, cyclohexyl, 1-tetrazolyl, 1-triazolyl, 1-pyrazolyl, 3-sydnonyl or 4-pyridylthio with the proviso that, wherein $R_2$ is any of the latter five groups, $R_3$ is hydrogen.

Preferred compounds of formula I are those wherein Y is a non-aromatic pyridonyl, pyrimidonyl, pyrazonyl, pyridazonyl or triazonyl group containing substitution on one or more members of the ring with the proviso that at least one nitrogen is substituted.

Examples of specific groups represented by Y in the above formula in accordance with the invention include the following:

2-oxopyridin-4-yl;

a 2-oxopyrimidin-4-yl group such as, for example, 1-amino, 1-ethyl- or 1-butoxy-1,2-dihydro-2-oxopyrimidin-4-yl or 1-butoxy-1,2-dihydro-5-methyl-2-oxopyrimidin-4-yl;

a 4-oxopyrimidin-2-yl group such as, for example, 1-ethyl-1,4-dihydro-6-methyl-4-oxopyrimidin-2-yl or 1,4-dimethyl-1,6-dihydro-6-oxopyrimidin-2-yl;

2,6-dioxopyrimidin-4-yl;

2-oxopyrazin-3-yl;

2,3,5-trioxopyrazinyl-6-yl;

3-oxopyridazin-6-yl;

3-oxopyridazin-4-yl;

a 5,6-dioxo-as-triazin-3-yl group such as, for example, 4-ethyl-, 4-methyl-4-allyl-, 4-butyl-, 4-(2-methoxyethyl)-, 1,4-dimethyl- or 1,4-diethyl-1,4,5,6-tetrahydro-5,6-dioxo-as-triazin-3-yl or 1,2,5,6-tetrahydro-1-ethyl-5,6-dioxo-as-triazin-3-yl;

2-oxotriazin-4-yl; or 2,4-dioxotriazin-6-yl.

In accordance with the invention, substituents on the nitrogen atoms in the heterocyclic ring represented by Y in formula I are selected from the group consisting of lower alkyl, lower alkenyl, lower alkynyl, cycloalkyl, hydroxy, lower alkoxy, amino, mono(lower alkyl)amino, di(lower alkyl)amino, formyl, lower alkanoyl, lower alkanoylamino, carbamoyl, mono(lower alkyl)aminocarbonyl and di(lower alkyl)aminocarbonyl.

Wherein in accordance with the invention, the heterocyclic ring represented by Y in formula I is substituted on the ring carbon atoms, such substituents are selected from the group consisting of lower alkyl, lower alkoxy, amino, mono(lower alkyl)amino, di(lower alkyl)amino, lower alkanoylamino, carboxy, lower alkoxycarbonyl, carbamoyl, mono(lower alkyl)aminocarbonyl, di(lower alkyl)aminocarbonyl, cyano and halogen.

Wherein either ring nitrogen or carbon atoms in the heterocyclic ring represented by Y in formula I are substituted by lower alkyl groups, said groups may in turn be substituted with a member selected from the group consisting of hydroxy, lower alkoxy, amino, mono(lower alkyl)amino, di(lower alkyl)amino, formyl, lower alkanoyl, lower alkanoylamino, carboxy, lower alkoxycarbonyl, carbamoyl, mono(lower alkyl)aminocarbonyl, di(lower alkyl)aminocarbonyl, cyano, halogen and epoxy.

In accordance with the present invention, the terms "lower alkyl", "lower alkenyl" and "lower alkynyl"

indicate both straight-and branched-chain hydrocarbon groups containing from one to six carbon atoms. Examples of such groups include methyl, ethyl, vinyl, allyl, ethynyl, propynyl and the like. Lower alkoxy groups contain in the alkyl portion thereof from one to six carbon atoms. Examples of such groups include methoxy, ethoxy, propoxy and the like. The term "lower alkanoyl" indicates those groups containing up to seven carbon atoms such as, for example, acetyl, propionyl and the like. Further in accordance with the invention, the term "cycloalkyl" indicates a cyclic hydrocarbon group containing from three to seven carbon atoms such as, for example, cyclopropyl, cyclohexyl and the like.

The following group of compounds is especially preferred in accordance with the present invention:

(7R)-3-[[(1,4,5,6-tetrahydro-4-ethyl-5,6-dioxo-as-triazin-3-yl)-thio]methyl]-7-[2-(2-thienyl)-acetamido]-3-cephem-4-carboxylic acid;

(7R)-3-[[1,4,5,6-tetrahydro-4-methyl-5,6-dioxo-as-triazin-3-yl)-thio]methyl]-7-[2-(2-thienyl)-acetamido]-3-cephem-4-carboxylic acid;

(7R)-3-[[1,4,5,6-tetrahydro-4-allyl-5,6-dioxo-as-triazin-3-yl)-thio]methyl]-7-[2-(2-thienyl)-acetamido]-3-cephem-4-carboxylic acid;

(7R)-3-[[1,4,5,6-tetrahydro-4-butyl-5,6-dioxo-as-triazin-3-yl)-thio]methyl]-7-[2-(2-thienyl)-acetamido]-3-cephem-4-carboxylic acid;

(7R)-3-[[(1,4,5,6-tetrahydro-4-(2-methoxyethyl)-5,6-dioxo-as-triazin-3-yl)-thio]methyl]-7-[2-(2-thienyl)-acetamido]-3-cephem-4-carboxylic acid;

(7R)-3-[[(1,4,5,6-tetrahydro-1,4-dimethyl-5,6-dioxo-as-triazin-3-yl)-thio]methyl]-7-[2-(2-thienyl)-acetamido]-3-cephem-4-carboxylic acid;

(7R)-3-[[(1-amino-1,2-dihydro-2-oxo-4-pyrimidinyl)-thio]methyl]-7-[2-(2-thienyl)-acetamido]-3-cephem-4-carboxylic acid;

(7R)-3-[[(1,4,5,6-tetrahydro-1,4-diethyl-5,6-dioxo-as-triazin-3-yl)-thio]methyl]-7-[2-(2-thienyl)-acetamido]-3-cephem-4-carboxylic acid;

(7R)-3-[[(1,2,5,6-tetrahydro-1-ethyl-5,6-dioxo-as-triazin-3-yl)-thio]methyl]-7-[2-(2-thienyl)-acetamido]-3-cephem-4-carboxylic acid;

(7S)-7-methoxy-3-[[(1,4,5,6-tetrahydro-4-methyl-5,6-dioxo-as-triazin-3-yl)thio]methyl]-7-[2-(thienyl)-acetamido]-3-cephem-4-carboxylic acid;

(7R)-3-[[(1-ethyl-1,2-dihydro-2-oxo-4-pyrimidinyl)-thio]methyl]-7-[2-(2-thienyl)-acetamido]-3-cephem-4-carboxylic acid;

(7R)-3-[[(1-butoxy-1,2-dihydro-2-oxo-4-pyrimidinyl)-thio]methyl]-7-[2-(2-thienyl)-acetamido]-3-cephem-4-carboxylic acid;

(7R)-3-[[(1-butoxy-1,2-dihydro-5-methyl-2-oxo-4-pyrimidinyl)-thio]methyl]-7-[2-(2-thienyl)-acetamido]-3-cephem-4-carboxylic acid;

(7R)-3-[[(1,4-dimethyl-1,6-dihydro-6-oxo-2-pyrimidinyl)-thio]methyl]-7-[2-(2-thienyl)-acetamido]-3-cephem-4-carboxylic acid;

(7R)-3-[[(1-ethyl-1,4-dihydro-6-methyl-4-oxo-2-pyrimidinyl)-thio]methyl]-7-[2-(2-thienyl)-acetamido]-3-cephem-4-carboxylic acid;

(7R)-7-(2-cyanoacetamido)-3-[[(1,4,5,6-tetrahydro-4-ethyl-5,6-dioxo-as-triazin-3-yl)-thio]methyl]-3-cephem-4-carboxylic acid;

(7R)-3-[[(1-amino-1,2-dihydro-2-oxo-4-pyrimidinyl)-thio]methyl]-7-[2-(3-sydnonyl)-acetamido]-3-cephem-4-carboxylic acid;

(7R)-3-[[(1-amino-1,2-dihydro-2-oxo-4-pyrimidinyl)-thio]methyl]-7-[2-(1-tetrazolyl)-acetamido]-3-cephem-4-carboxylic acid;

(7R)-3-[[(1,4,5,6-tetrahydro-4-ethyl-5,6-dioxo-as-triazin-3-yl)-thio]methyl]-7-[(R)-mandelamido]-3-cephem-4-carboxylic acid;

(7R)-7-[(R)-2-amino-2-phenylacetamido]-3-[[(1,4,5,6-tetrahydro-4-ethyl-5,6-dioxo-as-triazin-3-yl)-thio]methyl]-3-cephem-4-carboxylic acid;

(7R)-3-[[(1,4,5,6-tetrahydro-4-ethyl-5,6-dioxo-as-triazin-3-yl)-thio]methyl]-7-[2-(5-oxo-1,2,3-oxadiazolidin-3-yl)-acetamido]-3-cephem-4-carboxylic acid;

(7R)-3-[[(1-ethyl-1,2-dihydro-2-oxo-4-pyrimidinyl)-thio]-methyl]-7-[2-(5-oxo-1,2,3-oxadiazolidin-3-yl)-acetamido]-3-cephem-4-carboxylic acid;

(7R)-3-[[(1,4,5,6-tetrahydro-4-ethyl-5,6-dioxo-as-triazin-3-yl)-thio]methyl]-7-[2-(1-H-tetrazol-1-yl)-acetamido]-3-cephem-4-carboxylic acid;

(7R)-3-[[(1,4,5,6-tetrahydro-4-ethyl-5,6-dioxo-as-triazin-3-yl)-thio]methyl]-7-[(R)-2-hydroxyhexanamido]-3-cephem-4-carboxylic acid;

(7R)-3-[[(1,4,5,6-tetrahydro-4-ethyl-5,6-dioxo-as-triazin-3-yl)-thio]methyl]-7-[(R)-2-hydroxy-4-methyl-valeramido]-3-cephem-4-carboxylic acid;

(7R)-3-[[(1,4,5,6-tetrahydro-4-ethyl-5,6-dioxo-as-triazin-3-yl)-thio]methyl]-7-[(R)-2-hydroxy-2-(cyclohexyl-acetamido]-3-cephem-4-carboxylic acid; and (7R)-3-[[(1,4,5,6-tetrahydro-4-ethyl-5,6-dioxo-as-triazin-3-yl)-thio]methyl]-7-[2-(2-furyl)-acetamido]-3-cephem-4-carboxylic acid.

In accordance with the present invention, the compounds represented by formula I are prepared by reacting a compound represented by the general formula $$X'—W_1 \qquad \qquad II$$

wherein X' is a deacetoxycephalosporin moiety, the carboxyl group at position four thereof being in a protected form and $W_1$ is a leaving group with a compound represented by the general formula $$H—S—Y \qquad \qquad III$$

wherein X has the meaning given above and cleaving off the protecting group.

A second preparation in accordance with the present invention consists of reacting a compound represented by the general formula $$X''—S—Y \qquad \qquad IV$$

wherein Y has the meaning given above and X'' is a deacetoxycephalosporanyl group wherein the carboxyl group at position four is in a protected form with an acid represented by the general formula $$Z—OH \qquad \qquad V$$

wherein Z represents an acyl group which is the substituent on the amino group in the 7 position of the deacetoxycephalosporinyl group represented by X in formula I or with a reactive functional derivative thereof, and thereafter cleaving off the protecting group. If desired, the product may then be converted into a salt by conventional methods.

Examples of methods whereby the carboxyl group of the moiety represented by X' and X'' in formulas II and IV can be protected by salt formation with an inorganic or tertiary organic base such as, for example, triethylamine. After the reaction of the compounds of formulae II and IV with the compounds of formulae III and V, respectively, is completed, the protecting group can be removed by methods well known in the art. Where the carboxyl group is protected by salt formation, e.g., with triethylamine, the protecting group can be cleaved by treatment with acids such as, for example, hydrochloric acid, sulfuric acid, phosphoric acid, citric acid and the like at low temperatures, e.g., 0°–10° C.

Examples of the leaving group designated $W_1$ in formula II above include a halogen, e.g., chlorine, bromine or iodine, an acyloxy group such as, for example, a lower alkanoyloxy group such as acetoxy, a lower alkylsulfonyloxy group such as, for example, mesyloxy an arylsulfonyloxy group such as, for example, tosyl, an azido group and the like.

The reaction of a compound of formula II with a compound of formula III is carried out utilizing methods well known in the art. Thus, the reaction is carried out at a temperature between about 40° C. and 80° C., preferably at about 60° C. in water or a buffer solution of pH 6 to 7, preferably 6.5, for from 3 to 8, preferably 6, hours.

The reaction of a compound of formula IV with an acid of formula V or a reactive functional derivative thereof can likewise be carried out by conventional procedures. For example, a free acid of formula V is reacted with an ester of formula IV in the presence of a carbodiimide such as, for example, dicyclohexyl carbodiimide or an oxazolium salt such as, for example, N-ethyl-5-phenylisoxazolium-3'-sulfonate. Further, a salt of an acid of formula IV, e.g., a trialkylammonium salt, can be reacted with a reactive functional derivative of an acid of formula V. These reactions are carried out in an inert organic solvent such as, for example, ethyl acetate, acetonitrile, dioxane, chloroform, methylene chloride, benzene or dimethylformamide at a temperature of between about $-40°$ and $+5°$ C., preferably at 0° C.

Reactive functional derivatives of the acids of formula V include, for example, halides, i.e., chlorides, bromides and fluorides, azides, anhydrides, particularly mixed anhydrides with strong acids, reactive esters, e.g., N-hydroxysuccinimide esters, amides, e.g., imidazolides and the like.

The compounds of formula II above are known and can be prepared by methods known in the art from the corresponding cephalosporins, i.e., compounds represented by the general formula

wherein X is as defined above. Examples of such compounds include the alkali metal salts, e.g., the sodium salts of cephalothin, 7-alpha-methoxycephalothin, cephacetrile, (7R)-mandelamino-cephalosporanic acid and 7-(3-syndnonacetamido)-cephalosporanic acid and the zwitter-ion cephaloglycine.

Certain of the compounds of formula III are novel. The novel compounds of formula III can be prepared in a manner analogous to the preparation of the known compounds. Thus, a 1-substituted 2-oxo-4-mercaptopyridine can be prepared from a correspondingly-substituted 4-chloro-2-oxo-pyridine [Chem. Ber. 99, 255 (1966)] by nucleophilic exchange, e.g., with an alkali hydrogen sulfide. In a similar manner, a 1,3-disubstituted-2,6-dioxo-1,2,3,6-tetrahydro-4-mercaptopyrimidine can be prepared from a corresponding 4-chloro-2,6-dioxo-1,2,3,6-tetrahydropyrimidine. The 5,6-dioxo-3-mercapto-as-triazines can be prepared from the correspondingly-substituted thiosemicarbazides in an analogous manner to the synthesis of 1,4,5,6-tetrahydro-4-ethyl-5,6-dioxo-3-mercapto-as-triazine (see the dissertation of K. H. Ongania [Innsbruck 1972]). Finally, a thiol of formula III which contains a double-bond between the carbon atom substituted by the mercapto group and an adjacent nitrogen atom can be present as a tautomeric thioketone.

A compound of formula IV can be prepared by the reaction of a compound represented by the formula

wherein $X''$ and $W_1$ have the meanings given above with a compound of formula III under the conditions given above for the reaction of compounds of formulas II and III.

The acids of formula V and their reactive derivatives are known or are analogs of known compounds which can be prepared by conventional methods known to the art. The acids of formula V which contain an asymmetric carbon atom normally occur as racemic mixtures which can be separated into optically active isomers by conventional procedures. For example, an optically active resolving agent such as alpha, alpha-(1-naphthyl)-ethylamine or alpha-methylbenzylamine which react with the carboxyl group can be utilized to form diastereomers which can be separated by selective crystallization and converted into the corresponding optical isomers.

The compounds of formula I can likewise occur as optically pure isomers and as isomeric mixtures. A compound of formula I in the D form can be prepared by the conventional procedure of fractional crystallization of a salt such as the calcium salt or by reacting a compound of formula III with a compound of formula II in the D form or a compound of formula IV with an acid of formula V in the D form or a reactive functional derivative thereof. The latter method is preferred.

The compounds of formula I possess a broad spectrum of antibiotic activity against both gram-positive and gram-negative microorganisms. Their antibiotic and bactericidal activity allows them to be used therapeutically and as disinfectants. The compounds of formula I are particularly advantageous against penicillinase-positive Staphylococci as well as various cephalosporinase-positive gram-negative bacteria such as, for example, *Escherichia coli* and various species of Proteus, Klebsiella, Aerobacter and Serratia. It is contemplated, in the case of adults, a daily dosage of from about 1 to 4 grams is administered parenterally. This dosage regimen may be adjusted by the clinician as the therapeutic situation requires. The novel cephalosporin derivatives of the invention may also be administered orally, rectally or topically in suitable dosage forms and may be administered in the form of their pharmaceutically acceptable salts or hydrates. Parenteral administration is particularly preferred.

The compounds of formula I containing a free basic group, e.g., an amino group, form addition salts with organic and inorganic acids. Typical organic salts include, for example, alkylsulfonates, e.g., ethanesulfonates, monoarylsulfonates, e.g., toluenesulfonates and benzenesulfonates, acetates, tartrates, maleates, citrates, benzoates, salicylates, ascorbates and the like. Typical inorganic salts include, for example, the hydrohalides, e.g., hydrochloride and hydrobromide, sulfates, nitrates, phosphates and the like. The salts can also be hydrated, either during manufacture or by gradual hydration of an initially anhydrous salt due to the hydroscopic properties thereof.

The antimicrobial activity of two compounds representative of the compounds of formula I against E. coli and penicillin resistant and penicillin sensitive strain of Staphylococci is given in the following table. The results represent $CD_{50}$ values in the mouse upon subcutaneous injection. In the table, compound A is (7R)-3-[[(1,4,5,6-tetrahydro-4-ethyl-5,6-dioxo-as-triazin-3-yl)-thio]methyl]-7-[2-(5-oxo-1,2,3-oxadiazolidin-3-yl)-acetamido]-3-cephem-4-carboxylic acid sodium salt and compound B is (7R)-3-[[(1,4,5,6-tetrahydro-4-ethyl-5,6-dioxo-as-triazin-3-yl)-thio]methyl]-7-[2-(1-H-tetrazol-1-yl)-acetamido]-3-cephem-4-carboxylic acid sodium salt. The acute toxicity of these compounds ($LD_{50}$ i.v. in the mouse) is between 2000 and 4000 mg/kg for compound A and between 1000 and 2000 mg/kg for compound B.

TABLE

| Cmpd. | Staphylococcus aureus Schoch (Penicillin-sensitive) | Staphylococcus aureus 887 (Penicillin-sensitive) | Escherichia coli 1346 |
|---|---|---|---|
| A | 0.25 | 5.5 | 0.38 |
| B | 0.60 | 3.2 | 0.90 |

The compounds of formula I and their pharmaceutically acceptable salts can be used in the form of conventional pharmaceutical preparations; for example, the aforesaid compounds can be mixed with conventional organic or inorganic, inert pharmaceutical carrier materials suitable for parenteral or internal administration. They can be administered in conventional pharmaceutical forms, preferably parenteral forms, for example, solutions, suspensions and emulsions. Most preferably, the cephalosporins of the invention are prepared in a dry form, e.g., by lyophilization, suitable to be reconstituted for parenteral administration. Examples of conventional pharmaceutical carrier materials which may be utilized in such forms include, for example, water for injection, vegetable oils, polyalkylene glycols and the like. Such preparations can be subjected to conventional pharmaceutical expedients such as sterilization and can contain conventional pharmaceutical adjuncts such as preservatives, stabilizing agents, wetting agents, emulsifying agents, salts for the adjustments of osmotic pressure, buffers and the like. The compositions can also contain other therapeutically active materials.

The following Examples further illustrates the invention. All temperatures are in degrees centigrade.

EXAMPLE 1

A total of 120 g of 4-ethyl-thiosemicarbazide were reacted in the presence of 23 g of sodium in 1 liter of methanol for 4 hours with 116 g of oxalic acid dimethyl ester at the boiling point of the mixture. The product was isolated from the mixture as the sodium salt. The mixture was then acidified and 1,4,5,6-tetrahydro-4-ethyl-5,6-dioxo-3-mercapto-astriazine was obtained in aqueous solution, melting point 189°–190°.

4.4 Grams of cephalothin sodium $[[\alpha]_D^{20} = +130°$ (c=1 in water)] were stirred in 100 ml of water with 2.25 g of the 1,4,5,6-tetrahydro-4-ethyl-5,6-dioxo-3-mercapto-as-triazine obtained above and 1.05 g of sodium bicarbonate for 6 hours at 60° and pH ca 6.5 under a nitrogen atmosphere. The mixture was then cooled to 10° and adjusted to pH 2 with 2-N hydrochloric acid. The precipitate was filtered off under suction, washed with 25 ml of ice-water, dissolved in acetone and the resulting solution evaporated in vacuo. The residue was dissolved in dimethylformamide and the solution treated with 7.5 ml of a 2-N solution of the sodium salt of 2-ethyl-caproic acid in ethyl acetate. By dilution with ethyl acetate, the desired product crystallized out. The crystalline product was filtered off under suction, washed successively with ethyl acetate, ether and petroleum ether and dried in vacuo to yield 4.5 g (80%) of the sodium salt of (7R)-3-[[(1,4,5,6-tetrahydro-4-ethyl-5,6-dioxo-as-triazin-3-yl)-thio]methyl]-7-[2-(2-thienyl)-acetamido]-3-cephem-4-carboxylic acid; melting point 170° (decomposition); $[\alpha]_D^{20} = +13.1°$ (c=0.800 in water).

EXAMPLE 2

In a manner analogous to that described in Example 1, 1.91 g of 1,4,5,6-tetrahydro-4-methyl-5,6-dioxo-3-mercapto-as-triazine, mp 218°–220° (decomp.) prepared from 4-methylthiosemicarbazide and oxalic acid were reacted with 4.18 g of cephalothin sodium salt to yield 2.8 g (54.1%) the sodium salt of (7R)-3-[[(1,4,5,6-tetrahydro-4-methyl-5,6,-dioxo-as-triazin-3-yl)-thio]methyl]-7-[2-(2-thienyl)-acetamido]-3-cephem-4-carboxylic acid; melting point 200°–205° (decomposition); $[\alpha]_D^{20} = -2.7°$ (c=0.592 in water).

EXAMPLE 3

In a manner analogous to that described in Example 1 3.33 g of 1,4,5,6-tetrahydro-4-allyl-5,6-dioxo-3-mercapto-as-triazine, mp 138°–140°, prepared from 4-allyl-thiosemicarbazide and oxalic acid dimethyl ester were reacted with 6.29 g of cephalothin sodium salt to yield 3.0 g (36.8%) of the sodium salt of (7R)-3-[[(1,4,5,6-tetrahydro-4-allyl-5,6-dioxo-as-triazin-3-yl)-thio]methyl]-7-[2-(2-thienyl)-acetamido]-3-cephem-4-carboxylic acid; melting point 180° (decomposition); $[\alpha]_D^{20} = +19.7°$ (c=0.376 in water).

EXAMPLE 4

In a manner analogous that the described in Example 1 3.62 g of 1,4,5,6-tetrahydro-4-butyl-5,6-dioxo-3-mercapto-as-triazine, mp 180°–181°, prepared from 4-butyl-thiosemicarbazide and oxalic acid dimethyl ester, were reacted with 6.27 g of cephalothin sodium salt to give the sodium salt of (7R)-3-[[(1,4,5,6-tetrahydro-4-butyl-5,6-dioxo-as-triazin-3-yl)-thio]methyl]-7-[2-(2-thienyl-acetamido]-3-cephem-4-carboxylic acid; melting point 160° (decomposition); $[\alpha]_D^{20} = +17.6°$ (c=0.640 in water).

EXAMPLE 5

In a manner analogous to that described in Example 1 3.65 g of 1,4,5,6-tetrahydro-4-(2-methoxyethyl)-5,6-dioxo-3-mercapto-as-triazine, mp 158°–160°, prepared from 4-(2-methoxyethyl)-thiosemicarbazide and oxalic acid dimethyl ester were reacted with 6.27 g of cephalothin sodium salt to yield 2.0 g (23.8%); of the sodium salt of (7R)-3-[[(1,4,5,6-tetrahydro-4-(2-methoxyethyl)-5,6-dioxo-as-triazin-3-yl)-thio]methyl]-7-[2-(2-thienyl)-acetamido]-3-cephem-4-carboxylic acid (c=0.280 in water).

EXAMPLE 6

In a manner analogous to that described in Example 1 2.6 g of 1,4,5,6-tetrahydro-1,4-dimethyl-5,6-dioxo-3-mercapto-as-triazine, mp 231°–233° (decomposition), prepared from 1,4-dimethyl-thiosemicarbazide and oxalic acid dimethyl ester were reacted with 6.27 g of cephalothin sodium salt to yield 4.6 g (58.0%) of the sodium salt of (7R)-3-[[(1,4,5,6-tetrahydro-1,4-dimethyl-5,6-dioxo-as-triazin-3-yl)-thio]-methyl]-7-[2-(2-thienyl)-acetamido]-3-cephem-4-carboxylic acid); $[\alpha]_D^{20}=-9.55°$ (c=0.461 in water).

EXAMPLE 7

In a manner analogous to that described in Example 1 2.01 g of 1,4,5,6-tetrahydro-1,4-diethyl-5,6-dioxo-3-mercapto-as-triazine, mp 177°–170°, prepared from 1,4-diethyl-thiosemicarbazide and oxalic acid dimethyl ester were reacted with 6.27 g of cephalothin sodium salt to yield 5.5 g (65.7%) of the sodium salt of (7R)-3-[[1,4,5-6-tetrahydro-1,4-diethyl-5,6-dioxo-as-triazin-3-yl)-thio]methyl]-7-[2-(2-thienyl)-acetamido]-3-cephem-4-carboxylic acid; melting point 175° (decomposition); $[\alpha]_D^{20}=+10.2°$ (c=0.547 in water).

EXAMPLE 8

A total of 46.5 g of 1-ethyl-thiosemicarbazide were reacted in 700 ml of acetone at 40° with 48 g of oxalic acid monomethyl ester chloride. 34.3 Grams of the product were treated with 9.2 g of sodium methylate in 300 ml of methanol. The triazine was isolated from the mixture as the sodium salt. The mixture was then acidified and 1,2,5,6-tetrahydro-1-ethyl-5,6-dioxo-3-mercapto-as-triazine obtained in aqueous solution; melting point 213°–214° (decomposition).

In a manner analogous to that described in Example 1 10.45 g of cephalothin sodium salt were reacted with 4.8 g of the triazine obtained above to yield 7.0 g (52.6%); of the sodium salt of (7R)-3-[[(1,2,5,6-tetrahydro-1-ethyl-5,6-dioxo-as-triazin-3-yl)-thio]methyl]-7-[2-(2-thienyl)-acetamido]-3-cephem-4-carboxylic acid; melting point 210°–215° (decomposition); $[\alpha]_D^{20}=+8.85°$ (c=0.181 in water).

EXAMPLE 9

In a manner analogous to that described in Example 1 5.16 g of 7-α-methoxy-cephalothin sodium salt [$[\alpha]_D^{20}=+194.5°$ (c=0.308 in water)] was reacted with 1.82 g of 1,4,5,6-tetrahydro-4-methyl-5,6-dioxo-3-mercapto-as-triazine to give (7S)-7-methoxy-3-[[(1,4,5,6-tetrahydro-4-methyl-5,6-dioxo-as-triazin-3-yl)-thio]methyl]-7-[2-thienyl)-acetamido]-3-cephem-4-carboxylic acid as the sodium salt to yield 1.0 g (15.9%); $[\alpha]_D^{20}=+54.6°$ (c=0.308 in water).

EXAMPLE 10

In a manner analogous to that described in Example 1 4.18 g of cephalothin sodium salt was reacted with 1.8 g of 1-ethyl-1,2-dihydro-4-mercapto-2-oxo-pyrimidine to give (7R)-3-[[(1-ethyl-1,2-dihydro-2-oxo-4-pyrimidinyl)-thio]methyl]-7-[2-(2-thienyl)acetamido]-3-cephem-4-carboxylic acid as the sodium salt to yield 3.2 g (65.3%); melting point>190° (decomposition); $[\alpha]_D^{20}=-58)$ (c=0.570 in water).

EXAMPLE 11

In a manner analogous to that described in Example 1 4.18 g of cephalothin sodium salt was reacted with 2.2 g of 1-butoxy-1,2-dihydro-4-mercapto-2-oxo-pyrimidine, mp 99°–100°, prepared from of 1-butoxyuracil and phosphorus pentasulfide; to yield (7R)-3-[[(1-butoxy-1,2-dihydro-2-oxo-4-pyrimidinyl)thio]methyl]-7-[2-(2-thienyl)-acetamido]-3-cephem-4-carboxylic acid as the sodium salt; yield 3.8 g (70%); $[\alpha]_D^{20}=-6°$ (c=0.850 in water).

EXAMPLE 12

In a manner analogous to that described in Example 1 25 g of 1-butoxy-5-methyl-uracil prepared by reacting of butoxyurea with β,β-diethoxy-α-methylpropionic acid ester was reacted with 50 g of phosphorus pentasulfide to give 1-butoxy-1,2-dihydro-4-mercapto-5-methyl-2-oxo-pyrimidine;

In a manner analogous to that described in Example 1 3.36 g of the thus-obtained pyrimidine was reacted with 6.0 g of cephalothin sodium salt to give (7R)-3-[(1-butoxy-1,2-dihydro-5-methyl-2-oxo-4-pyrimidinyl)-thio]methyl-7-[2-(2-thienyl)-acetamido]-3-cephem-4-carboxylic acid; yield 0,8 g (9,7%); melting point>170° (decomposition).

EXAMPLE 13

In a manner analogous to that described in Example 1 4.18 g of cephalothin sodium salt were reacted with 1.8 g of 1,4-dimethyl-1,6-dihydro-2-mercapto-6-dihydro-2-mercapto-6-oxo-pyrimidine to give (7R)-3-[[(1,4-dimethyl-1,6-dihydro-6-oxo-2-pyrimidinyl)-thio]methyl]-7-[2-2-thienyl)-acetamido]-3-cephem-4-carboxylic acid as the sodium salt to yield 1.35 g (26.3%); melting point 200°–210° (decomposition); $[\alpha]_D^{20}=+9.5°$ (c=0.348 in water).

EXAMPLE 14

18 Grams of N-ethyl-thiourea were dissolved in 50 m. of glacial acetic acid, boiled to reflux and treated dropwise with 17.2 g of diketene. The mixture was then boiled at reflux for 20 minutes and subsequently evaporated to 50 ml. While cooling and stirring, the residue was treated with 50 ml of water. The yellowish crystals which precipitated were filtered off under suction and recrystallized from tetrahydrofuran to give 1-ethyl-1,4-dihydro-2-mercapto-6-methyl-4-oxo-pyrimidine; melting point 190°.

In a manner analogous to that described in Example 1, 6.27 g of cephalothin sodium salt were reacted with 2.98 g 1-ethyl-1,4-dihydro-2-mercapto-6-methyl-4-oxo-pyrimidine, to give (7R)-3-[[(1-ethyl,1,4-dihydro-6-methyl-4-oxo-2-pyrimidinyl)-thio]methyl]-7-[2-(2-thienyl)-acetamido]-3-cephem-4-carboxylic acid as the sodium salt to yield 3.2 g (40.4%); melting point 170° (decomposition); $[\alpha]_D^{20}=14.4°$ (c=0.333 in methanol).

EXAMPLE 15

In a manner analogous to that described in Example 1 9.5 g of cephacetrile sodium salt was reacted with 5.46 g of 1,4,5,6-tetrahydro-4-ethyl-5,6-dioxo-3-mercapto-as-triazine to give (7R)-7-(2-cyanacetamido)-3-[[(1,4,5,6-tetrahydro-4-ethyl-5,6-dioxo-as-triazin-3-yl)-thio]methyl]-3-cephem-4-carboxylic acid as the sodium salt to yield 3.3 g (26.8%); $[\alpha]_D^{20}=+7.85°$ (c=0.1785 in water).

EXAMPLE 16

In a manner analogous to that described in Example 1 8.0 g of the sodium salt of (7R)-mandelamido-cephalosporanic acid and 3.72 g of 1,4,5,6-tetrahydro-4-ethyl- 5,6-dioxo-3-mercapto-as-triazine were reacted to give (7R)-3-[[1,4,5,6-tetrahydro-4-ethyl-5,6-dioxo-as-triazin-3-yl)-thio]methyl]-7-[(R)-mandelamido]-3-cephem-4-carboxylic acid as the sodium salt to yield 1.7 g (16.8%); $[\alpha]_D^{20} = -19.6°$ (c = 0.500 in water).

EXAMPLE 17

In a manner analogous to that described in Example 1 8.1 g of cephaloglycine and 3.78 g of 1,4,5,6-tetrahydro-4-ethyl-5,6-dioxo-3-mercapto-as-triazine were reacted to yield 4.19 g (40.5%); of (7R)-7-[(R)-2-amino-2-phenylacetamido]-3-[[(1,4,5,6-tetrahydro-4-ethyl-5,6-dioxo-as-triazin-3-yl)-thio]methyl]-3-cephem-4-carboxylic acid which was isolated as a Zwitter ion; yield 4.19 g (40.5% melting point > 180° (decomposition); $[\alpha]_D^{20} = -86.3$) (c = 0.276 in dimethylformamide).

EXAMPLE 18

In a manner analogous to that described in Example 1 7.7 g of the sodium salt of 7-(3-sydnonacetamido)-cephalosporanic acid and 3.46 g of 1,4,5,6-tetrahydro-4-ethyl-5,6-dioxo-3-mercapto-as-triazine were reacted to give (7R)-3-[[(1,4,5,6-tetrahydro-4-ethyl-5,6-dioxo-as-triazin-3-yl)-thio]methyl]-7-[2-(5-oxo-1,2,3-oxadiazolidin-3-yl)-acetamido]-3-cephem-4-carboxylic acid as the sodium salt; to yield 3.3 g (31%); melting point > 210° (decomposition): $[\alpha]_D^{20} = +17.9°$ (c = 0.380 in water).

EXAMPLE 19

In a manner analogous to that described in Example 1 11.6 g of the sodium salt of 7-(3-sydnonacetamido)-cephalosporanic acid and 4.7 g of 1-ethyl-1,2-dihydro-4-mercapto-2-oxo pyrimidine were reacted to give (7R)-3-[[(1-ethyl-1,2,-dihydro-2-oxo-4-pyrimidinyl)-thio]methyl]-7-[2-(5-oxo-1,2,3-oxadiazolidin-3-yl)acetamido]-3-cephem-4-carboxylic acid as the sodium salt; yield 3.6 g (23.2%); $[\alpha]_D^{20} = -43.7°$ (c = 0.600 in water).

EXAMPLE 20

A total of 2.72 g of 7-amino-cephalosporanic acid was suspended in 100 ml of water together with 1,4,5,6-tetrahydro-4-ethyl-5,6-dioxo-3-mercapto-as-triazine. The suspension was treated with 1.85 g of sodium bicarbonate to yield a solution having a pH of 6.4. The solution was stirred for 3 hours at 60° while gassing with nitrogen, then cooled to 20° and stirred under nitrogen for a further 1 hour with addition of 1 g of active carbon. After filtration, the filtrate was adjusted to pH 3.8 with 2-N hydrochloric acid, cooled to 0° and stirred for 1 hour. The crystals which separated were filtered off under suction, washed successively with a small amount of ice-water, acetone, ether and petroleum ether and dried at 50° in a high vaccum to give 7-amino-3-desacetoxy-3-[(1,4-5,6-tetrahydro-4-ethyl-4,6-dioxo-as triazine-3-yl)-thio]-cephalosporanic acid; yield 2.3 g (60%) of beige powder of melting point 230°-235° (decomposition).

In an alternate synthesis of the above compound 5.1 g of 7-amino-3-azido-3-desacetoxy-cephalosporanic acid were stirred for 6 hours at 60° while gassing with nitrogen, together with 5.16 g of 1,4,5,6-tetrahydro-4-ethyl-5,6-dioxo-3-mercapto-as-triazine and 4.2 g of sodium bicarbonate in 200 ml of a buffer of pH 7.0. The solution was cooled to 25° and adjusted to pH 3.5 with 2-N hydrochloric acid. The crystals which separated were filtered off under suction (2.2 g). Concentration of the mother liquor yielded a further 1.7 g; total yield 3.9 g (50%).

1.28 Grams of tetrazole-1-acetic acid were dissolved in a mixture of 50 ml of tetrahydrofuran and 5 ml of dimethylformamide. The resulting solution was treated at −20° successively with 1.18 ml of N-methyl-morpholine and 1.4 ml of chloroformic acid isobutyl ester and subsequently stirred for 20 additional minutes at a temperature between −10° and −20°. To this mixture was added an ice-cold solution in 50 ml of water of the salt obtained by reacting 3.85 g of 7-amino-3-descacetoxy-3-[(1,4,5,6-tetrahydro-4-ethyl-5,6-dioxo-as-triazin-3-yl)-thio]-cephalosporanic acid and 1.4 ml of triethylamine. The mixture was then stirred for 30 minutes at 0° and for 1 hour at 20°. Subsequently, the mixture was concentrated in vacuo and the aqueous phase acidified with 5 ml of 2-N hydrochloric acid. whereby the product precipitated out as a crude acid. The latter was filtered off under suction, washed with excess ethyl acetate and dissolved in dimethylformamide. The solution was treated with a 2-N solution of the sodium salt of 2-ethylcaproic acid in ethyl acetate and subsequently diluted with ethanol and ether, whereby the desired crude sodium salt (3.3 g) precipitated out. For purification, the crude sodium salt was dissolved in 20 ml of water and treated with 60 ml of ethanol, after which a dark resin precipitated and was rejected. The filtrate was evaporated in vacuo and the residue treated with ethanol and ether to yield 2.3 g (44.5%) of pure (7R)-3-[[(1,4,5,6-tetrahydro-4-ethyl-5,6-dioxo-as-triazin-3-yl)-thio]methyl]-7-[2-(1-H-tetrazol-1-yl)-acetamido]-3-cephem-4-carboxylic acid as the sodium salt as a light-beige powder, melting point 210° (decomposition); $[\alpha]_D^{20} = +23°$ (c = 0.824 in water).

EXAMPLE 21

4,4 Grams of 7-amino-3-desacetoxy-3-[(1,4,5,6-tetrahydro-4-ethyl-5,6-dioxo-as-triazin-3-yl)-thio]-cephalosporanic acid were dissolved at 0° in a mixture of 44 ml of water and 44 ml of acetone by the addition of 2.5 g of potassium bicarbonate with stirring. There was then added dropwise at 0° while stirring, a solution of 3 g of (R)-2-dichloroacetoxy-n-caproic acid chloride (boiling point$_{0.5}$ = 75°–76°) in 30 ml of acetone. The mixture was then stirred for 2 hours at 0° and for 1 hour at 20°. The acetone was distilled off from the filtered solution at 30° under reduced pressure. The aqueous solution was stirred for 45 minutes at pH 9.5 by the addition of potassium carbonate, then extracted twice with ethyl acetate and adjusted to a pH of 1.5–2.0 with 3-N sulfuric acid. After extraction with ethyl acetate with addition of dimethylformamide, the ethyl acetate solution was washed several times with a 10% sodium chloride solution, dried over magnesium sulfate and evaporated under reduced pressure at 25°. The residue was dissolved in 100 ml of isopropanol and treated with 12 ml of a 2-N solution of the sodium salt of 2-ethyl caproic acid in isopropanol. The desired crude sodium salt was filtered off under suction, reprecipitated from water/isopropanol and dried under reduced pressure. The pure sodium salt of (7R)-3-[[(1,4,5,6-tetrahydro-4-5,6-dioxo-as-triazin-3-yl)-thio]methyl]-7-[(R)-2-hydroxyhexanamido]-3-cephem-4-carboxylic acid was obtained as a bridge powder; yield 56%; melting point from 183° (decomposition); $[\alpha]_D^{25} = +8.2°$ (c = 1.00 in water).

EXAMPLE 22

In a manner analogous to that described in Example 21 3.5 g of 7-amino-3-desacetoxy-3-[(1,4,5,6-tetrahydro- 4-ethyl-5,6-dioxo-as-triazin-3-yl)-thio]-cephalosporanic acid were reacted with 2.4 g of (R)-2-dichloroacetoxy-isocaproic acid chloride (boiling point $_{0.2}$=63°–64°) to yield; (7R)-3-[[(1,4,5,6-tetrahydro-4-ethyl-5,6-dioxo-as-triazin-3-yl)-thio]methyl]-7-[(R)-2-hydroxy-4-methyl-veleramido]-3-cephem-4-carboxylic acid as the sodium salt yield 51%; melting point from 180° (decomposition); $[\alpha]_D^{25}$= +6.0° (c=1.00 in water).

EXAMPLE 23

In a manner analogous to that described in Example 21 3.9 g of 7-amino-3-desacetoxy-3-[(1,4,5,6-tetrahydro-4-ethyl-5,6-dioxo-as-triazin-3-yl)-thio]-cephalosporanic acid were reacted with 2.9 g of (R)-2-dichloroacetoxy-2-cyclohexyl-acetyl chloride (boiling point$_{0.5}$=105°–107°)*(7R)-3-[[(1,4,5,6-tetrahydro-4-ethyl-5,6-dioxo-as-triazin-3-yl)-thio]methyl]-7-[(R)-2-hydroxy-2-cyclohexyl-acetamido]-3-cephem-4-carboxylic acid as the sodium salt; yield 37%; melting point from 190° (decomposition); $[\alpha]_D^{25}$= +2.8° (c=0.50 in water).

EXAMPLE 24

3.85 Grams of 7-amino-3-desacetoxy-3-[1,4,5,6-tetrahydro-4-ethyl-5,6-dioxo-as-triazin-3-61)-thio]-cephalosporanic acid were dissolved at 0° in a mixture of 40 ml of water and 40 ml of acetone by the addition of 2.4 g of potassium bicarbonate and stirring. To this solution there was added dropwise at −5°, a solution of 1.45 g of 2-(2-furyl)-acetyl chloride in 15 ml of acetone and the mixture stirred for 3 hours at −5° and for 1.5 hours at 20°. The solution was extracted twice with ethyl acetate and the aqueous phase acidified at 0° with 3-N sulfuric acid to a pH value of 2. After extraction with ethyl acetate with addition of dimethylformamide, the ethyl acetate solution was washed three times with a 10% sodium chloride solution, dried over magnesium sulfate and evaporated under reduced pressure at 25°. The residue was dissolved in methanol and treated with 8 ml of a 2-N solution of the sodium salt of 2-ethyl-caproic acid in isopropanol. The desired crude sodium salt was precipitated with diethyl ether, filtered off under suction, washed with diethyl ether and then recrystallized from water with addition of acetone. There was obtained (7R)-3-[[(1,4,5,6-tetrahydro-4-ethyl-5,6-dioxo-as-triazin-3-yl)-thio]methyl]-7-[2-(2-furyl)acetamido]-3-cephem-4-carboxylic acid as the sodium salt, a beige powder: yield 43%; melting point from 180° (decomposition); $[\alpha]_D^{25}$= +18.4° (c=1.0 in water).

EXAMPLE 25

In a manner analogous to that described in Example 1 8.36 g of cephalothin sodium salt were reacted with 3.0 g of 1-amino-1,2-dihydro-4-mercapto-2-oxo-pyridine to give (7R)-3-[[(1-amino-1,2-dihydro-2-oxo-4-pyrimidinyl)-thio]methyl]-7-[2-(2-thienyl)-acetamido]-3-cephem-4-carboxylic acid as the sodium salt; yield 4.1 g (40.2%); melting point>185° (decomposition); $[\alpha]_D^{20}$=78.5° (c=0.439 in water). The pyrimidine was prepared by reacting 1-benzylideneaminouracil [melting point 220°–223°]; Literature: Monatshefte für Chemie 96, 1735 (1965) with 12 g of phosphorus pentasulfide in pyridine, followed by hydrolysis with hydrochloric acid.

EXAMPLE 26

In a manner analogous to that described in Example 1 8.26 g of cephalothin sodium salt were reacted with 3.34 g of 1,2,5,6-tetrahydro-5,6-dioxo-3-mercapto-2-methyl-as-triazine to give (7R)-3-[[(1,2,5,6-tetrahydro-2-methyl-5,6-dioxo-as-triazin-3-yl)-thio]methyl]-7-[2-(2-thienyl)-acetamido]-3-cephem-4-carboxylic acid as the sodium salt; yield 5.8 g (56%); melting point 185° (decomposition); $[\alpha]_D^{20}$= −49.3 (c=0.450 in water). The triazine was prepared in a manner analogous to that described in Example 1 by reacting 31.5 g of 2-methyl-thiosemicarbazide and 35.4 g of oxalic acid dimethyl ester; melting point 260°.

EXAMPLE 27

In a manner analogous to that described in Example 1 8.26 g of cephalothin sodium salt were reacted with 2.98 g of 1,2-dihydro-4-mercapto-1-methyl-2-oxo-pyrimidine to give (7R)-3-[[(1,2-dihydro-1-methyl-2-oxo-4-pyrimidinyl)-thio]methyl]-7-[2-(2-thienyl)-acetamido]-3-cephem-4-carboxylic acid as the sodium salt; yield 7.3 g (62.4%); melting point 180° (decomposition); $[\alpha]_D^{20}$= −67.7° (c=0.604 in water).

EXAMPLE 28

In a manner analogous to that described in Example 1 8.36 g of cephalothin sodium salt were reacted with 3.32 g of 1,3-dihydro-4-mercapto-1-methoxy-2-oxo-pyrimidine to give (7R)-3-[[(1,2-dihydro-1-methoxy-2-oxo-4-pyrimidinyl)-thio]methyl]-7-[2-(2-thienyl)-acetamido]-3-cephem-4-carboxylic acid as the sodium salt; $[\alpha]_D^{20}$= −90.6° (c=0.338 in water). The pyrimidine was prepared in a manner analogous to that described in Example 11 by reaction of 1-methoxyuracil and 18 g of phosphorus pentasulfide; melting point 177°.

EXAMPLE 29

In a manner analogous to that described in Example 1 6.27 g of cephalothin sodium salt were reacted with 2.75 g of 1-ethoxy-1,2-dihydro-4-mercapto-2-oxo-pyrimidine to give (7R)-3-[[(1-ethoxy-1,2-dihydro-2-oxo-4-pyrimidinyl)-thio]methyl]-7-[2-(2-thienyl)-acetamido]-3-cephem-4-carboxylic acid as the sodium salt; yield 3.5 g (44%); melting point 180° (decomposition); $[\alpha_D^{20}$= −74.2° (c=0.525 in water). The pyrimidine starting material was prepared in a manner analogous to that described in Example 11 by reacting 6.4 g of 1-ethoxyuracil and 18 g of phosphorus pentasulfide; melting point 119°–120°.

EXAMPLE 30

In a manner analogous to that described in Example 1 1.25 g of cephalothin sodium salt were reacted with 0.470 g of 1,6-dihydro-3-mercapto-1-methyl-6-oxo-pyridazine to give (7R)-3-[[(1,6-dihydro-1-methyl-6-oxo-3-pyridazinyl)-thio]methyl]-7-[2-(2-thienyl)-acetamido]-3-cephem-4-carboxylic acid as the sodium salt; yield 1.0 g (66.7%); melting point>215° (decomposition); $[\alpha]_D^{20}$= −49.7° (c=0.332 in water). The pyridazine starting material was prepared by reacting 2.88 g of 3-chloro-1,6-dihydro-1-methyl-6-oxo-pyridazine [melting point 91°–92°]; Literature: Monatshefte für Chemie 99, 33 (1968)] and 5.88 g of sodium hydrosulfide in ethanol at 130° and 5–7 atmospheres; melting point 115°.

EXAMPLE 31

In a manner analogous to that described in Example 20 9.5 g of sydnono-3-acetic acid were reacted with 21.4 g of 7-amino-3-desacetoxy-3-[(1-amino-1,2-dihydro-2-oxo-pyrimidin-4-yl)-thio]cephalosporanic acid to give (7R)-3-[[(1-amino-1,2-dihydro-2-oxo-4-pyrimidinyl)-thio]methyl]-7-[2-(3-sydnonyl)acetamido]-3-cephem-4-carboxylic acid as the sodium salt; yield 9.7 g (32%); melting point from 200° (decomposition); $[\alpha]_D^{20} = -61.3°$ (c=0.5 in water).

EXAMPLE 32

In a manner analogous to that described in Example 1 24.5 g of D-p-hydroxy-N-tert.butyl-oxycarbonyl-cephaloglycine were reacted with 8.66 g of 1,4,5,6-tetrahydro-4-ethyl-5,6-dioxo-3-mercapto-as-triazine with subsequent removal of the tert.butyloxycarbonyl protecting group with formic acid to give (7R)-7-[(R)-2-amino-2-(p-hydroxyphenyl)-acetamido]-3-[[(4-ethyl-1,4,5,6-tetrahydro-5,6-dioxo-as-triazin-3-yl)-thio]methyl]-3-cephem-4-carboxylic acid; yield 5.7 g (23%); melting point from 200° (decomposition); $[\alpha]_D^{20} = 79.8°$ (c=0.3 in dimethylformamide).

EXAMPLE 33

In a manner analogous to that described in Example 1 6.0 g of cephapirin were reacted with 2.56 g of 1,4,5,6-tetrahydro-4-ethyl-5,6-dioxo-3-mercapto-as-triazine to give (7R)-3-[[(4-ethyl-1,4,5,6-tetrahydro-5,6-dioxo-as-triazin-3-yl)-thio]methyl]-7-[2-(4-pyridyl-thio)-acetamido]-3-cephem-4-carboxylic acid as the sodium salt; yield 1.9 g (26%); melting point form 205° (decomposition); $[\alpha]_D^{20} = +36.2°$ (c=0.5 in water).

EXAMPLE 34

In a manner analogous to that described in Example 1 6 g of (pyrazol-1-yl-methyl)-cephalosporin sodium salt were reacted with 3.12 g of 1,4,5,6-tetrahydro-4-ethyl-5,6-dioxo-3-mercapto-as-triazine to give (7R)-3-[[(4-ethyl-1,4,5,6-tetrahydro-5,6-dioxo-as-triazin-3-yl)-thio]methyl]-7-(2-pyraczol-1-yl-acetamido)-3-cephem-4-carboxylic acid as the sodium salt; yield 4.0 g (51%); melting point from 190° (decomposition).

EXAMPLE 35

A solution of 76 g of thiourea in 1000 ml of dimethylformamide was treated with 65.4 ml of methyl isocyanate and then stirred for 72 hours at 50°-55°. The solution was then evaporated in vacuo and the residue recystallized from water; yield 79.5 g (60%) of colourless 5-methyl-2-thio-biuret melting point 209°-210°.

A solution of 14.8 g of sodium in 1000 ml of methanol was treated with 39.9 g of 5-methyl-2-thio-biuret and 72 g of diethylcarbonate and boiled at reflux for 25 hours. The solution was concentrated to a volume of 200 ml in vacuo. The substance which crystallized out was filtered off under suction, dissolved in 200 ml of water and acidified with 2-N hydrochloric acid. The precipitated compound was filtered off under suction and recrystallized from 350 ml of ethanol; yield 11.2 g (23%) of colorless substance; melting point 275°.

In a manner analogous to that described in Example 1 8.36 g of cephalothin sodium salt were reacted with 3.34 g of 1,2,3,6-tetrahydro-2,6-dioxo-4-mercapto-1-methyl-s-triazine prepared above to give (7R)-3-[[(1,2,3,6-tetrahydro-2,6-dioxo-1-methyl-s-triazin-4-yl)-thio]methyl]-7-[2-(2-thienyl)-acetamido]-3-cephem-4-carboxylic acid as the sodium salt yield 5.5 g (53%); melting point from 220° (decomposition); $[\alpha]_D^{20} = -43°$ (c=0.1 in water).

EXAMPLE 36

44 Grams of N-ethylurea and 105 g of $\beta,\beta$-diethoxypropionic acid ethyl ester were added to a solution of 15.0 g of sodium in 700 ml of ethanol. The yellow solution was then heated for 3 hours at 25° and subsequently boiled under reflux for 15 hours. The mixture was evaporated in vacuo and the residue dissolved in 300 ml of water, cooled to 0° and acidified with 100 ml of concentrated hydrochloric acid. A crystalline intermediate precipitated out (43 g) and was filtered off under vacuum, washed with 100 ml of ice-water and subsequently heated to 80°-100° in 250 ml of water until conversion into the desired water-soluble 1-ethyl-uracil is complete. The solution was evaporated in vacuo at 40° and the remaining residue recrystallized from ethanol/ether; yield 14.0 g (20%) of colorless 1-ethyl-uracil; melting point 150° C.

Chlorine was led into a solution of 9.9 g of 1-ethyl-uracil in 150 ml of glacial acetic acid until iodine-potassium-starch paper reacted positively and 1-ethyl-uracil was no longer detectable by thin-layer chromatography (ca. 0.5 hours). The mixture was evaporated in vacuo at 40° and the crystalline residue recrystallized from 300 ml of ethanol; yield 10.0 g (81%) of colorless, fine needles of 1-ethyl-5-chlorouracil; melting point 244°-247°.

1.74 Grams of 1-ethyl-5-chlorouracil were mixed with 4.44 g of phosphorus pentasulfide and 0.1 ml of water and the mixture treated with 30 ml of pyridine and boiled at reflux for 3.75 hours. The mixture was then evaporated in vacuo at 40°, the residue suspended in 30 ml of water and treated with 30 ml of 2-N hydrochloric acid. The crystals obtained were filtered off under suction, washed with water and recrystallized from 1-ethyl-5-chloro-1,2-dihydro-4-mercapto-2-oxo-pyrimidine; melting point 217°-220°.

In a manner analogous to that described in Example 1 6.27 g of cephalothin sodium salt were reacted 3.04 g of 1-ethyl-5-chloro-1,2-dihydro-4-mercapto-2-oxo-pyrimidine prepared above to give (7R)-3-[[(1-ethyl-5-chloro-1,2-dihydro-2-oxo-4-pyrimidinyl)-thio]methyl]-7-[2-(2-thienyl)-acetamido]-3-cephem-4-carboxylic acid as the sodium salt; yield 3.5 g (42%); melting point from 185° (decomposition); $[\alpha]_D^{20} = -95.2°$ (c=0.394 in water).

EXAMPLE 37

In a manner analogous to that described in Example 20 2.95 g of tetrazol-1-acetic acid were reacted with 8.55 g of 7-amino-3-[(1,2,5,6-tetrahydro-2-methyl-5,6-dioxo-as-triazin-3-yl)-thio]-cephalosporanic acid to give (7R)-3-[[(1,2,5,6-tetrahydro-2-methyl-5,6-dioxo-as-triazin-3-yl)-thio]methyl]-7-[2-(1-H-tetrazol-1-yl)-acetamido]-3-cephem-4-carboxylic acid as the sodium salt; yield 4.65 g (40%); melting point 220°-230° (decomposition); $[\alpha]_D^{20} = 53.6°$ (c=0.321 in water).

EXAMPLE 38

In a manner analogous to that described in Example 21 9.25 g of D-O-dichloroacetyl-mandelic acid chloride were reacted with 11.1 g of 7-amino-3-desacetoxy-3-[(1,2,5,6-tetrahydro-2-methyl-5,6-dioxo-as-triazin-3-yl)-thio]-cephalosporanic acid to give (7R)-7-(R)-mandelamido-3-[[(1,2,5,6-tetrahydro-2-methyl-5,6-dioxo-as-triazin-3-yl-thio]methyl]-3-cephem-4-carboxylic acid as the sodium salt; yield 4.3 g (27%); melting point 200°-210° (decomposition); $[\alpha]_D^{20} = 66.8°$ (c=0.296 in water).

EXAMPLE 39

In a manner analogous to that described in Example 20 5.76 g of sydnono-3-acetic acid were reacted with 14.95 g of 7-amino-3-desacetoxy-3-[(1,2,5,6-tetrahydro- 2-methyl-5,6-dioxo-as-triazin-3-yl)-thio]-cephalosporanic acid to give (7R)-7-[2-(3-sydnonyl)-acetamido]-3-[[(1,2,5,6-tetrahydro-2-methyl-5-,6-dioxo-as-triazine-3-yl)-thio]methyl]-3-cephem-4-carboxylic acid as the sodium salt; yield 7.0 g (33%); melting point from 200° (decomposition); $[\alpha]_D^{20} = -25.5°$ (c=0.227%).

EXAMPLE 40

In a manner analogous to that described in Example 1 3.34 g of cephalothin sodium salt were reacted with 1.42 g of of 1,2-dihydro-1-dimethylamino-4-mercapto-2-oxo-pyrimidine to give; (7R)-3-[[(1-dimethyl-amino-1,2-dihydro-2-oxo-4-pyrimidinyl)-thio]methyl]-7-[2-(2-thienyl)-acetamido]-3-cephem-4-carboxylic acid as the sodium salt; yield 2.4 g (57%); melting point from 165° (decomposition); $[\alpha]_D^{20} = -65.2°$ (c=0.557 in water).

EXAMPLE 41

67.75 Grams of 3,4-dichloro-6-hydroxy-pyridazine were dissolved in 205 ml of a 2-N sodium hydroxide solution and treated dropwise with 36 ml of dimethylsulfate. The mixture was then heated at 70° for 0.5 hour, cooled and extracted twice with chloroform. The combined chloroform extracts were washed with water, dried over sodium sulfate and evaporated in vacuo. The residue is recrystallized from high boiling petroleum ether; yield 54 g of 3,4-dichloro-1,6-dihydro-1-methyl-6-oxo-pyridazine (73%); melting point 97°.

A solution of 17.9 g of the 3,4-dichloro-1,6-dihydro-1-methyl-6-oxo-pyridazine prepared above in 200 ml of methanol was treated with a solution of 14.8 g of sodium hydrosulfide monohydrate in 200 ml of methanol. The mixture was then stirred for 1.5 hours at 25° while gassing with nitrogen. Undissolved material was then filtered off and the filtrate concentrated in vacuo. The residue was suspended in 150 ml of water, made acidic with 1-N hydrochloric acid and extracted three times with ethyl acetate. The combined ethyl acetate extracts were washed with water, dried over sodium sulfate and evaporated in vacuo. The residue obtained was recrystallized from ethanol; yield 9 g of yellowish needles of 3-chloro-1,6-dihydro-4-mercapto-1-methyl-6-oxopyridazine; melting point 163°.

In a manner analogous to that described in Example 1 8.36 g of cephalothin sodium salt were reacted with 3.7 g of 3-chloro-1,6-dihydro-4-mercapto-1-methyl-6-oxo-pyridazine prepared above to give (7R)-3-[[3-chloro-1,6-dihydro-1-methyl-6-oxo-4-pyridazinyl)-thio]methyl]-7-[2-(2-thienyl)-acetamido]-3-cephem-4-carboxylic acid as the sodium salt; melting point 225°-230° (decomposition); $[\alpha]_D^{20} = +5.35°$ (c=0.522 in water).

EXAMPLE 42

In a manner analogous to that described in Example 1 7.55 g of cephalothin sodium salt were reacted with 2.95 g of 1,2-dihydro-1,6-dimethyl-4-mercapto-2-oxopyridine to give (7R)-3-[[(1,2-dihydro-1,6-dimethyl-2-oxo-4-pyridyl)-thio]methyl]-7-[2-(2-thienyl)-acetamido]-3-cephem-4-carboxylic acid as the sodium salt; yield 3.0 g (31%); melting point 178°-185° (decomposition); $[\alpha]_D^{20} = +46.2°$ (c=0.353 in water).

EXAMPLE 43

In a manner analogous to that described in Example 1 8.24 g of cephaloram sodium salt were reacted with 3.63 g of 1,4,5,6,-tetrahydro-4-ethyl-5,6-dioxo-3-mercapto-as-triazine to give (7R)-3-[[(4-ethyl-1,4,5,6-tetrahydro-5,6-dioxo-as-triazin-3-yl)-thio]methyl]-7-(2-phenylacetamido)-3-cephem-4-carboxylic acid as the sodium salt; yield 2.2 g (21%); melting point 190°-200° (decomposition); $[\alpha]_D^{20} = +19.8°$ (c=0.339 in water).

EXAMPLE 44

The (7R)-7-[(RS)-2-bromo-2-phenylacetamido]-3-[(1,4,5,6-tetrahydro-4-ethyl-5,6-dioxo-as-triazin-3-yl)-thio]methyl-3-cephem-4-carboxylic acid sodium salt was prepared in a manner analogous to that described in Example 21 from 23.1 g of 7-amino-3-desacetopy-3-[(1,4,5,6-tetrahydro-4-ethyl-5,6-dioxo-as-triazin-3-yl)-thio]-cephalosporanic acid and 14.0 g of DL-α-bromophenylacetic acid chloride; yield 10 g (28%); melting point from 190° (decomposition).

EXAMPLE 45

23.7 Grams of 1-ethyl-3-chloro-1,2-dihydro-2-oxopyrazine were added to a solution of 22.2 g of sodium hydrosulfide monohydrate in 1000 ml of methanol and the mixture stirred for 3 hours at 25°. The precipitated sodium chloride was then filtered off and the yellow filtrate evaporated in vacuo at 40°. The residue was recrystallized from ethanol; yield 8.0 g (34%) of crude yellow substance. For purification, 5.0 g of the latter were suspended in 50 ml of 0.5-N hydrochloric acid and strongly acidified with addition of 10 ml of 2-N hydrochloric acid. The mixture was stirred for 10 minutes at 25° and subsequently stored overnight in a refrigerator.

The resulting orange-yellow crystals 1-ethyl-1,2-dihydro-3-mercapto-2-oxo-pyrazine (3.65 g) were filtered off under bacuum, washed with a small amount of ice-water and dried in vacuo at 50°; melting point 204°-206° (decomposition).

In a manner analogous to that described in Example 1 6.27 g of cephalothin sodium salt were reacted with 2.50 g of 1-ethyl-1,2-dihydro-3-mercapto-2-oxo-pyrazine prepared above to give (7R)-3-[[(1-ethyl-1,2-dihydro-2-oxo-3-pyrazinyl)-thio]methyl]-7-[2-(2-thienyl)-acetamido]-3-cephem-4-carboxylic acid as the sodium salt; yield 5.0 g (65%); melting point from 175° (decomposition); $[\alpha]_D^{20} = +12.2°$ (c=0.5 in water).

EXAMPLE 46

4.0 grams of (7R)-3-azidomethyl-7-[2-(2-thienyl)-acetamido]-3-cephem-4-carboxylic acid sodium salt [melting point from 170° (decomposition); $[\alpha]_D^{20} = +134.4°$ (c=0.5 in water)] 2.07 g of 1,4,5,6-tetrahydro-4-ethyl-5,6-dioxo-3-mercapto-as-triazine and 1.01 g of sodium bicarbonate were combined in 100 ml of a buffer solution of pH 7.0 and stirred for 24 hours at 50°-55° while gassing with nitrogen.

The mixture was then cooled to 25° and adjusted to pH 2 with 2-N hydrochloric acid. The crude acid which precipitated was filtered off under suction, washed with water and then stirred for 10 minutes in 100 ml of ethyl acetate. The purified acid was filtered of under suction (1.3 g), suspended in 25 ml of methanol and treated with 2.5 ml of a 2-N solution of 2-ethylcaproic acid sodium salt in ethyl acetate, a solution resulting. By dilution with 100 ml of ethyl acetate, the sodium salt of (7R)-3-[(1,4,5,6-tetrahydro-4-ethyl-5,6-dioxo-as-triazin-3-yl)thio]methyl-7-[2-(2-thienyl)-acetamido]-3-cephem-4-carboxylic acid precipitated out; yield 1.25 g (24%); identical in all characteristics with the product manufactured according to Example 1.

EXAMPLE 47

In a manner analogous to that described in Example 20 6,4 g (tertrazolyl)-acetic acid and 17,75 g 7-amino-3-desacetoxy-3-[(1-amino-1,2-dihydro-2-dihydro-2-oxopyrimidin-4-yl)-thio]-cephalosporanic were reacted to give (7R)-3-[[(1-amino-1,2-dihydro-2-oxo-4-pyrimidinyl)-thio]-methyl]-7-[2-(1-tetrazolyl)-acetamido]-4-carboxylic acid as the sodium salt; yield 8.0 g (33%); melting point from 190° (decomposition).

EXAMPLE 48

Reconstitutable preparations for intramuscular injection were prepared by lyophilizing and hermetically sealing ampoules each containing 2,5 ml of a sterile solution of 1 gram of the sodium salt of (7R)-3-[[(1,4,5,6-tetrahydro-4-ethyl-5,6-dioxoas-triazin-3-yl)-thio]methyl]-7-[2-(1-H-tetrazol-1-yl)-acetamido]-3-cephem-4-carboxylic acid. The contents of the ampoule are reconstituted with 2.5 ml of a sterile 2% solution of lidocaine hydrochloride before prior to administration.

EXAMPLE 49

Ampoules were prepared according to the manner described in Example 47 containing 1 gram of the sodium salt of (7R)-3-[[(1,4,5,6-tetrahydro-4-ethyl-5,6-dioxo-as-triazin-3-yl)-thio]methyl]-7-[2-(5-oxo-1,2,3-oxadiazolidin-3-yl)-acetamido]-3-cephem-4-carboxylic acid.

We claim:

1. A compound of the formula:

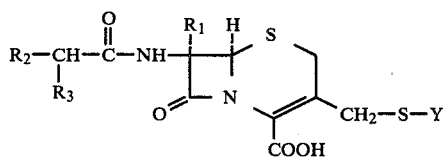

wherein Y is a 5,6-dioxo-as-triazin-3-yl group where at least one nitrogen atom in said triazinyl group is substituted with a member selected from the group consisting of lower alkyl, lower alkenyl, lower alkynyl, cycloalkyl, hydroxyl, lower alkoxy, amino, mono(lower alkyl)amino, di(lower alkyl)amino, formyl lower alkanoyl, lower alkanoylamino, carbamoyl, mono(lower alkyl)aminocarbonyl and di(lower alkyl)aminocarbonyl; $R_1$ is hydrogen or methoxy, $R_3$ is hydrogen, hydroxy, hydroxymethyl, amino, azido, carboxy or sulfo; $R_2$ is cyano, or a substituent selected from the group consisting of pyridylthio, alkyl containing from 1 to 6 carbon atoms, alkenyl containing from 2 to 6 carbon atoms, saturated or unsaturated non-aromatic cyclic hydrocarbon containing from 3 to 6 carbon atoms, phenyl, phenylalkyl or phenoxyalkyl wherein said substituent can be unsubstituted or substituted with one or more members selected from the group consisting of hydroxy, halo, lower alkyl or lower alkoxy; with the proviso that when $R_2$ is pyridylthio, $R_3$ is hydrogen; and pharmaceutically acceptable salts thereof and hydrates thereof.

2. A compound of the formula:

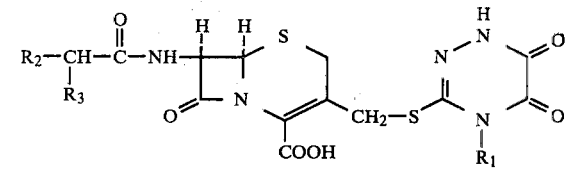

wherein $R_1$ is lower alkyl; $R_2$ is phenyl or phenyl substituted with hydroxy, halo, lower alkyl having 1 to 3 carbon atoms, or lower alkoxy containing 1 to 4 carbon atoms; and $R_3$ is hydrogen, hydroxy, sulfo, amino or carboxy or salts thereof.

3. A compound of the formula:

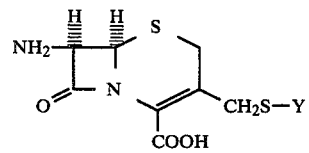

wherein Y is a 5,6-dioxo-as-triazin-3-yl group where at least one nitrogen atom in said triazinyl group is substituted with a member selected from the group consisting of lower alkyl, lower alkenyl, lower alkynyl, cycloalkyl, hydroxy, lower alkoxy, amino, mono(lower alkyl)amino, di(lower alkyl)amino, formyl lower alkanoyl, lower alkanoylamino, carbamoyl, mono(lower alkyl)aminocarbonyl and di(lower alkyl)aminocarbonyl; or pharmaceutically acceptable salts thereof and hydrates thereof.

4. The compound of claim 3 wherein Y is a 1,2,5,6-tetrahydro-2-lower alkyl-5,6-dioxo-as-triazin-3-yl.

5. The compound of claim 4 wherein said compound is 7-amino-3-desacetoxy-3[(1,2,5,6-tetrahydro-2-methyl-5,6-dioxo-as-triazin-3-yl)-thio]-cephalosporonic acid or salts thereof.

6. A compound in accordance with claim 1 wherein said compound is (7R)-7-(2-Cyanoacetamido)-3-[[(1,4,5,6-tetrahydro-4l-ethyl-5,6-dioxo-as-triazin-3-yl)-thio]methyl]-3-cephem-4-carboxylic acid.

7. A compound in accordance with claim 1 wherein said compound is (7R)-3-[[(1,4,5,6-Tetrahydro-4-ethyl-5,6-dioxo-as-triazin-3-yl)-thio]methyl]-7-[(R)-mandelamido]-3-cephem-4-carboxylic acid.

8. A compound in accordance with claim 1 wherein said compound is (7R)-7-[(R)-2-Amino-2-phenylacetamido]-3-[[(1,4,5,6-tetrahydro-4-ethyl-5,6-dioxo-as-triazin-3-yl)-thio]methyl]-3-cephem-4-carboxylic acid.

9. A compound in accordance with claim 1 wherein said compound is (7R)-3-[[(1,4,5,6-Tetrahydro-4-ethyl-5,6-dioxo-as-triazin-3-yl)-thio]methyl]-7-[(R)-2-hydroxyhexanamido]-3-cephem-4-carboxylic acid.

10. A compound in accordance with claim 1 wherein said compound is (7R)-3-[[(1,4,5,6-Tetrahydro-4-ethyl-5,6-dioxo-as-triazin-3-yl)-thio]methyl]-7-[(R)-2-hydroxy-4-methyl-valeramido]-3-cephem-4-carboxylic acid.

11. A compound in accordance with claim 1 wherein said compound is (7R)-3-[[(1,4,5,6-Tetrahydro-4-ethyl-5,6-dioxo-as-triazin-3-yl)-thio]methyl]-7-[(R)-7-hydroxy-2-(cyclohexyl)acetamido]-3-cephem-4-carboxylic acid.

12. The compound of claim 1 wherein said compound is (7R)-7-(R)mandelamido-3-[(1,2,5,6-tetrahydro-2- methyl-5,6-dioxo-as-triazin-3-yl)thio]-methyl 3-chem-4-carboxylic acid or pharmaceutically acceptable salts thereof.
13. A compound of claim 3 having the formula:
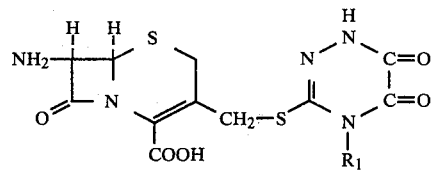
wherein $R_1$ is lower alkyl or salts thereof.
* * * * *